(12) United States Patent
Tanno et al.

(10) Patent No.: US 6,872,336 B2
(45) Date of Patent: Mar. 29, 2005

(54) PROCESS FOR PRODUCING A PHARMACEUTICAL SOLID PREPARATION CONTAINING A POORLY SOLUBLE DRUG

(75) Inventors: Fumie Tanno, Niigata-ken (JP); Yuichi Nishiyama, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 309 days.

(21) Appl. No.: 10/232,631

(22) Filed: Aug. 30, 2002

(65) Prior Publication Data

US 2003/0044528 A1 Mar. 6, 2003

(30) Foreign Application Priority Data

Sep. 5, 2001 (JP) ........................... 2001-268341

(51) Int. Cl.[7] ................................................. B29B 9/00
(52) U.S. Cl. ............................... 264/7; 264/13; 264/14; 264/117; 427/2.14; 427/2.15; 427/2.16
(58) Field of Search ............................. 264/7, 11–14, 264/117; 427/212, 213, 2.14, 2.15, 2.16

(56) References Cited

U.S. PATENT DOCUMENTS

| | | | |
|---|---|---|---|
| 3,494,780 A | | 2/1970 | Skiens ........................ 427/353 |
| 4,267,138 A | * | 5/1981 | Dobo et al. .................. 264/117 |
| 5,543,099 A | * | 8/1996 | Zhang et al. ................ 264/115 |
| 5,837,291 A | * | 11/1998 | Maruyama et al. .......... 424/489 |
| 6,132,772 A | * | 10/2000 | Sherman ..................... 424/489 |
| 6,375,873 B1 | * | 4/2002 | Lockemann et al. ........... 264/7 |
| 2002/0041934 A1 | * | 4/2002 | Nishiyama et al. .......... 427/421 |

FOREIGN PATENT DOCUMENTS

| | | |
|---|---|---|
| EP | 0 546 846 | 6/1993 |
| EP | 0 781 549 | 7/1997 |
| EP | 1 181 983 | 2/2002 |
| JP | 57085316 | 5/1982 |
| JP | 57 085316 | 5/1982 |
| JP | 58077811 | 5/1983 |
| JP | 2000281561 | 10/2000 |

* cited by examiner

Primary Examiner—Mary Lynn Theisen
(74) Attorney, Agent, or Firm—Alston & Bird LLP

(57) ABSTRACT

Among the conventional processes for producing solid dispersion, the solid dispersion obtained by a solvent method is excellent in terms of solubility and bioavailability of a poorly soluble drug. However, due to frequent uses of organic solvents in the solvent method, problems have arisen such as organic solvent residue in products, environmental pollution and operational safety as well as corporate problems such as capital investment and the like required to avoid such events. The present invention provides a process for preparing pharmaceutical solid preparations without use of organic solvents frequently used in conventional solvent methods. Specifically, the present invention provides a process for producing a pharmaceutical solid preparation, which is formulated by spraying a solution wherein a poorly soluble drug is dissolved in a plasticizer, and an aqueous solution and/or water dispersion of a water-soluble polymer from nozzle outlets simultaneously and separately in the process for producing the pharmaceutical solid preparation.

6 Claims, 2 Drawing Sheets

PROCESS FOR PRODUCING A PHARMACEUTICAL SOLID PREPARATION CONTAINING A POORLY SOLUBLE DRUG

BACKGROUND OF THE INVENTION

1. Field of the Invention

The present invention relates to a pharmaceutical solid preparation containing a poorly soluble drug for the purpose of improvement of dissolution and a process for the production thereof, and more particularly, to the pharmaceutical solid preparation obtained by delivering and discharging/spraying an aqueous solution and/or a water dispersion of a water soluble polymer as well as a plasticizer solution wherein a poorly soluble drug is dissolved, from nozzle outlets simultaneously and separately, and the process for the production thereof.

2. Description of the Invention

In light of efficiency and safety, it has been regarded as important that significantly high bioavailability is set in the designs for pharmaceutical solid preparations. One of important factors which affect bioavailability of medicines includes solubility of drugs, and numerous studies have been carried out regarding the relationship of solubility and digestive tract absorption. In particular, it has been known that the dissolution behavior of a poorly soluble drug is a key determinant of its oral bioavailability. Various methods have been studied for formulation techniques of solubility improvement in poorly soluble drugs, and among them, a solid dispersion element method has shown promise. This method is defined as a method in which a single molecular drug is dispersed in an inert carrier of a drug in a solid state. Several methods have been proposed for the process of production, and especially, a solvent method and a mixed pulverization method are included as practical methods.

The solvent method is a method for producing a solid dispersion by dissolving a drug and a water-soluble polymer which is a carrier in a solvent such as an organic solvent, and subsequently distilling off the solvent, or by dissolving the drug in the solvent, dispersing in the carrier followed by distilling off the solvent. It is believed that solubility and bioavailability can be improved because the drug becomes amorphous by dissolving the poorly soluble drug in the solvent and is dispersed in the carrier in such a state.

As specific examples of the solvent method, Japanese Patent Publication (JP-B) Nos. 3-1288/1991 and 3-28404/1991 have reported that the solid dispersion is obtained as follows. Lactose or the like is granulated with a water-soluble polymer such as hydroxypropylcellulose to make fine particles. Nifedipine which is a poorly soluble drug and a polymer base such as poly(vinylpyrrolidone), hydroxypropylmethylcellulose and methylcellulose are dissolved in the organic solvent to form a solution. The solution was sprayed on the fine particles. The sprayed particles are dried to yield the solid dispersion. Also, in Japanese Patent Provisional Publication (JP-A) No. 281561/2000, the solid dispersion is prepared by dissolving a poorly soluble drug such as cycloheptadines and the water-soluble polymer such as poly(vinylpyrrolidone), hydroxypropylmethylcellulose and hydroxypropylcellulose in a water/alcohol system, and subsequently spraying on lactose followed by granulating.

SUMMARY OF THE INVENTION

Among conventional methods for producing solid dispersions, those obtained by the solvent method are excellent in terms of solubility and bioavailability of the poorly soluble drug. However, in this solvent method, because organic solvents such as dichloromethane, acetone and alcohol are frequently used, considerable problems have arisen, including problems of organic solvents residue in products, environmental pollution by organic solvents and safety in operation, and corporate problems such as capital investment required to avoid such concerns.

As a result of an intensive study to solve the above problems, the present inventors have found a method for preparing a pharmaceutical solid preparation without use of an organic solvent which is frequently used in the conventional solvent method. That is, the inventors have found that a pharmaceutical solid preparation which is excellent in dissolution improvement of a drug can be made by being formulated by spraying an aqueous solution and/or water dispersion of a water-soluble polymer as well as a plasticizer solution in which a poorly soluble drug is dissolved from nozzle outlets simultaneously and separately in the pharmaceutical solid preparation. The formulation includes spray granulation and coating treatment of the preparation. For example, granulated materials or coated particles obtained by granulation or coating treatment become pharmaceutical solid preparations which are excellent in dissolution improvement of the drug. According to the present invention, the pharmaceutical solid preparation can be prepared without use of a conventional organic solvent and by using existing equipment and techniques. Also, it was confirmed that the resultant pharmaceutical solid preparation affords a similar improvement effect of dissolution as those of the conventional solvent methods.

According to the present invention, a solid solution preparation of a poorly soluble drug can be simply prepared using the existing equipment and without use of an organic solvent. Also, preparation of the present invention has the improved dissolution of a poorly soluble drug compared to the solid dispersion obtained by the conventional physically mixed method, and has solubility equivalent to the solid dispersion obtained by the conventional solvent method.

DETAILED DESCRIPTION OF THE PREFERRED EMBODIMENTS

Figure 1:
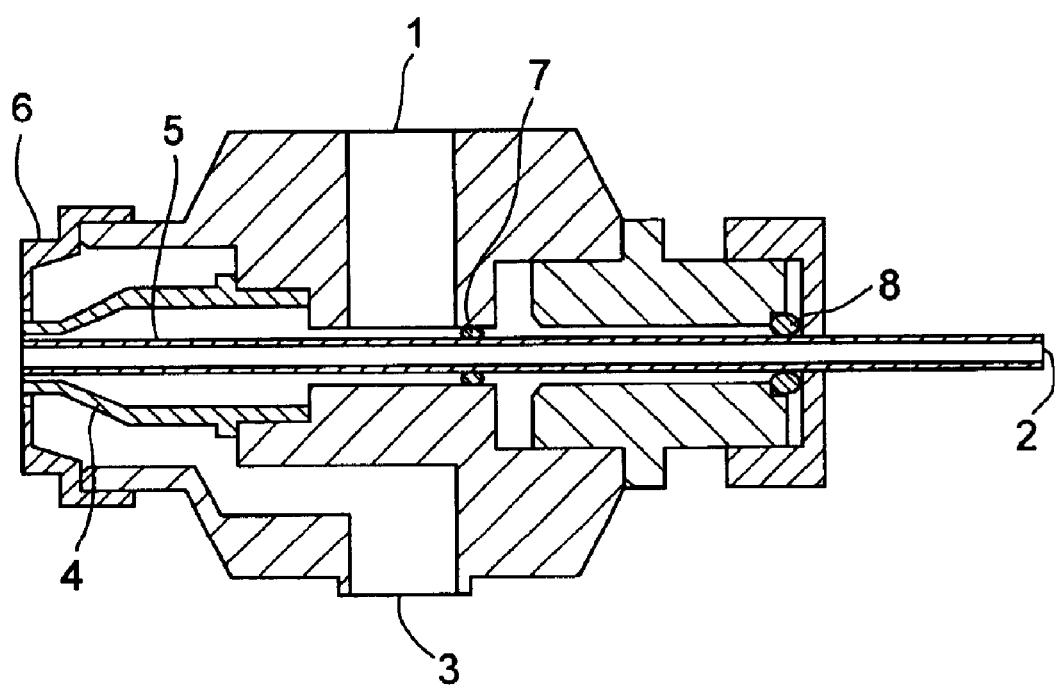
FIG. 1 shows a cross-sectional drawing of the three fluid nozzle used in a step of fluid bed granulation.

The poorly soluble drug used in the present invention is a drug of which solubility in water is extremely low and of which absorbability is inferior in normal oral administration, and is referred to, for example, as the drug defined as "nearly insoluble" or "extremely difficult to be dissolved" in Japanese Pharmacopoeia. In Japanese Pharmacopoeia, the solubility of a drug is defined as the degree of dissolvability within 30 minutes when the drug is placed in a solvent and shaken for 30 seconds every 5 minutes at 20±5° C. after making powder in the case of the drug being solid. "Nearly insoluble" is referred to the characteristic where an amount of 10,000 ml or more of the solvent is required to dissolve 1 g or 1 ml of the drug. "Extremely difficult to be dissolved" is referred to the characteristic where a solvent amount of 1,000 to 10,000 ml is required to dissolve 1 g or 1 ml of the drug. Specifically, for example, such drugs include nifedipine, phenacetin, phenytoin, digitoxin, nilvadipine, diazepam, griseofulvin and chloramphenicol.

Plasticizers used in the present invention include propylene glycol, polyethylene glycol, triethyl citrate, acetyl monoglyceride, glycerine, tributyl citrate, triacetin, diacetin, monoacetin and diethyl phthalate, which may be used alone or in combination of two or more.

These plasticizers are added aiming at improving the plasticity of polymer films and added for the purpose of improving the uniformity of granulations or coating films. Amounts are not especially limited as long as it is an additional amount required to achieve the purpose. However, it is desirable that the minimum weight part to significantly dissolve the drug in the plasticizer is added ranging from 1 to 20 weight parts, preferably from 7 to 15 weight parts based on one weight parts of the drug used.

The solution in which the drug used in the present invention is dissolved in the plasticizer is preferably the solution in which the drug and the plasticizer are dissolved at the above weight ratio. However, surfactants, oils, fats or the like can be included for the purpose of further improving the solubility of the drug.

The water-soluble polymers used in the present invention include, for example, cellulose derivatives such as methylcellulose, hydroxypropylcellulose, hydroxypropylmethylcellulose, hydroxypropylmethylcellulose phthalate, hydroxypropylmethylcellulose acetate succinate, ethylcellulose, hydroxyethylcellulose and sodium carboxymethylcellulose; poly(vinylpyrrolidone); and poly(vinyl alcohol). Among them, hydroxypropylmethylcellulose acetate succinate, hydroxypropylmethylcellulose phthalate, hydroxypropylmethylcellulose and poly(vinylpyrrolidone) are polymers effective for dissolution of the drug. Also, a mixture of these water-soluble polymers can be used as appropriate.

The fineness of these water-soluble polymers is not especially limited as long as it does not block up a spray gun when used as a dispersion, and the average particle diameter may be 100 $\mu$m or less, and preferably 50 $\mu$m or less.

The aqueous solutions of the water-soluble polymers include the aqueous solution obtained by dissolving in a weak alkali aqueous solution such as an ammonia solution. It is desirable that the solution is prepared at 5 to 30% by weight. In the dispersion of the water-soluble polymer, said polymer can be dispersed in a given amount of water with stirring, and the concentration is not especially limited but a concentration at 5 to 30% by weight may be preferred.

The combination ratio of the poorly soluble drug to the water-soluble polymer in the pharmaceutical solid preparation of the present invention is appropriately determined depending on the types of the poorly soluble drug and water-soluble polymer. It may be from (1:0.1) to (1:10), and preferably from (1:0.5) to (1:5) as a weight ratio. When the combination ratio of the water-soluble polymer is lower, recrystallization of the drug may be precipitated in the pharmaceutical solid preparation resulting in lowering the dissolution. When it is higher, it may not be preferable because dissolution may not be significantly improved and the pharmaceutical solid preparation may be bulky leading to increased dosages.

Formulation of the present invention includes coating treatment and spray granulation of the preparation. The types of preparations subjected to coating are not especially limited, but solid preparation such as tablets, granules or capsules may be preferable for performing uniform coating. Those subjected to spray granulation include powder bodies and nuclei of lactose, sucrose, glucose, trehalose, fructose, dextrin, starch, pullulan, carboxymethylcellulose and salts thereof, carboxymethylstarch and salts thereof, cellulose, poly(vinylalcohol) and hemicellulose.

The amount of coating varies depending on the types of solid preparation. An amount of 3 to 50% by weight as the solid content may be preferable based on the weight of the solid preparation. In the case of coating the solid preparation, coating of the solid preparation may be carried out using another coating agent such as hydroxypropylmethylcellulose prior thereto.

The process for producing the solid dispersion preparation of the present invention can advantageously produce the pharmaceutical solid preparation when, for example, the spray gun shown in FIG. 1 is used.

This has a construction such that the water-soluble polymer dispersion and/or the water-soluble polymer solution and the plasticizer solution are appropriately selected and inserted via a pump through a liquid A inlet 1 and a liquid B inlet 2, respectively. The liquid A inlet 1 and liquid B inlet 2 are linked to a nozzle outlet of A nozzle 4 and a nozzle outlet of B nozzle 5, respectively, and liquid A and B are discharged/sprayed. Air from an air inlet 3 is discharged through a nozzle outlet of an air nozzle (cap) 6. In FIG. 1, the nozzle outlets of A nozzle 4, B nozzle 5 and air are in approximately concentric circles and arranged from the inside to the outside. FIG. 1 also shows an O ring 7 and a gasket 8. There may be an embodiment where the water-soluble polymer dispersion and/or water-soluble polymer solution is used as liquid A and the plasticizer solution is used as liquid B. Conversely, there may be also an embodiment in which the plasticizer solution is used as liquid A and the water-soluble polymer dispersion and/or water-soluble polymer solution is used as liquid B.

The pump to insert the water-soluble polymer dispersion and/or water-soluble polymer solution and the plasticizer solution is not especially limited, and a commonly available one is used. It may be preferable to use a gear pump or a tube pump.

Materials of the spray gun used in the present invention are not especially limited as long as they are water-proof and are not dissolved and melted in the plasticizer at a temperature from room temperature to around 100° C. Heat-resistant materials such as stainless steel, which resists rust, and silicone may be preferable.

The shape and diameter of the nozzle are not especially limited as long as they are capable of spraying. A diameter for ease in spraying or a distance of 0.1 to 5 mm between the tube walls may be preferred.

The rate of the delivered solution from the spray gun is not especially limited, but the rate of a few g/min to some 100 g/min may be preferred as a rough standard to be easily formulated in general. There may be no concerns even in the case of a construction where air or gas for spraying can be supplied to the nozzle. The supplied amount of air or gas is not especially limited as long as it is in a range capable of spraying, but the amount of some 10 liters/min to some 100 liters/min may be preferable. Types of gas other than air are not especially limited, but a inert gas such as nitrogen or helium which is less interactive with the drug may be preferable.

By using this spray gun, common formulation machines equipped with the system to spray/dry the liquid may be used as such.

Fluid bed granulation equipment, pan coating equipment, coating equipment incorporated with a ventilation dry system, and fluid coating equipment can be used as equipment for formulation.

In order to further make the prepared solid preparation into tablets, those usually used thereafter in the field of preparations, other than the poorly soluble drug and water-soluble polymer, for example, an excipient such as lactose, corn starch, crystalline cellulose, D-mannitol and erythritol; a disintegrant such as low substituted hydroxypropyl cellulose, cross carmellose sodium, carmellose calcium and cross povidone; a pigment; perfume; a sweetener; may appropriately be added to the pharmaceutical solid preparation of the present invention if necessary.

Examples and Comparative Examples are shown below, and the present invention is described in detail, but the invention is not limited thereto.

EXAMPLE 1

The poorly soluble drug, nifedipine (10 g) (supplied by Daito Co., Ltd.) was dissolved in a mixture solution of the plasticizer, polyethylene glycol 400 (96 g) and triethyl citrate (4 g) to make Spray A solution. As the water-soluble polymer solution, a dispersion made of 6 g of talc, 0.2 g of sodium lauryl sulfate and 107.1 g of purified water for 20 g of hydroxypropylmethylcellulose acetate succinate (HPMCAS) (AS-MF: supplied by Shin-Etsu Chemical Co. Ltd.) was prepared to make Spray B solution. Lactose (200 g) (lactose 200M: supplied by DMV Co., Ltd.) was fluidized in a fluidized-bed granulation machine (equipment name: Multiplex: supplied by Freund Industrial Co., Ltd.: Multiplex MP-01), and both Spray A and B solutions were sprayed to granulate in a manner of side spraying using three fluid nozzles (spray gun) shown in FIG. 1. Spray A solution, Spray B solution and compressed air were supplied to three fluid nozzles by a tube pump from the outside. Solutions A and B and compressed air were passed through the solution lead-in path A and B nozzles and the air lead-in path (cap), respectively, and were sprayed as spray solutions which spread over concentric circles.

After granulation, the granules were selected by a 14-mesh sieve to yield preparation containing nifedipine.

The manipulation condition was as follows.

Spray gun: identical to the spray gun shown in FIG. 1. One having an internal diameter of 2.5 mm as A nozzle and one having an external diameter of 2.0 mm and the internal diameter of 1.0 mm as B nozzle were used.

Temperature of Spray A and B solutions: 27° C.

Dry air temperature: 70 to 80° C.

Rate of supplying air to the spray gun: 2.5 liters/min

Rate of supplying Spray A solution: 5 g/min

Rate of supplying Spray B solution: 4.1 g/min

Manipulation: 40 minutes

Used amount of HPMCAS: 2 fold by weight based on major component (nifedipine)

EXAMPLE 2

Granulation was carried out to obtain the nifedipine containing preparation in the same manner as that in Example 1, except that the aqueous solution of the water-soluble polymer was made by dissolving 20 g of hydroxypropylmethylcellulose (TC-5R: supplied by Shin-Etsu Chemical Co. Ltd.) in 180 g of purified water to render Spray B solution.

EXAMPLE 3

Granulation was carried out to obtain the nifedipine containing preparation in the same manner as that in Example 1, except that 200 g of lactose in Example 1 were replaced with the mixed powder of 170 g of lactose and 30 g of Hydrated Silicon-Dioxide (Carplex #80: supplied by Shionogi & Co. Ltd.).

Comparative Example 1

10 g of Nifedipine and 20 g of hydroxypropylmethylcellulose acetate succinate were dissolved in 300 g of mixed solvents of dichloromethane and ethanol (weight ratio 1:1) to render a spray solution. Lactose (200 g) was fluidized in a fluid bed granulation machine, and the spray solution was sprayed to granulate in the manner of side spraying followed by being selected by a 14-mesh sieve to yield a preparation containing nifedipine.

Comparative Example 2

10 g of Nifedipine, 20 g of hydroxypropylmethylcellulose acetate succinate and 200 g of lactose were mixed in a mortar to yield the nifedipine containing preparation physically mixed and powdered.

Test Example

The following test was carried out for the preparations of Examples 1 to 3 and Comparative Examples 1 and 2.

(1) Samples: preparations of Examples 1 to 3 and Comparative Examples 1 and 2.

(2) Test method: as the test solution, 500 ml of the second solution (pH 6.8) described in Japanese Pharmacopoeia was used. Each sample corresponding to 10 mg of nifedipine was added thereto, and a test was carried out according to the second method of the dissolution test method (paddle method) of Japanese Pharmacopoeia. The rotational frequency of the paddle was 100 rpm. For each constant time elapsed (0, 10, 20, 40, 80 minutes), 2 ml of solution was collected, to which a second solution was added up to a total volume of 10 ml to dilute 5 times. Subsequently, the dissolution amount of nifedipine was determined by measuring an absorbance at wavelengths of 325 nm and 500 nm using an automatic dissolution tester (Shimadzu UV-160: supplied by Shimadzu Corporation).

For an evaluation of dissolution rate improvements, those which provided a supersaturated solubility which exceeds the saturated solubility of nifedipine (10 mg/ml) and showed an dissolution rate of 75% or more of the drug in preparation in the results of the above dissolution test were considered "good".

Figure 2:
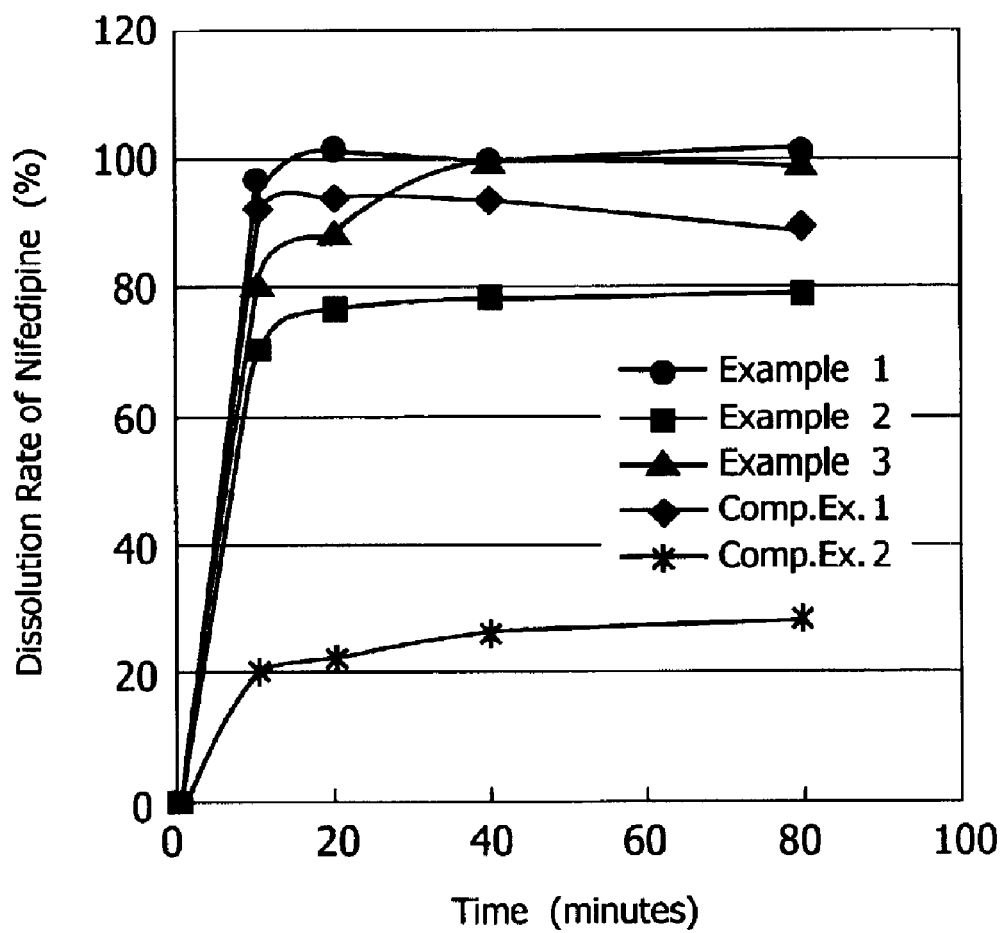
FIG. 2 shows the changes (average values) of dissolution rate of nifedipine with correlation to time from Examples 1 to 3 and Comparative Examples 1 and 2.

(3) Results of the test: changes of dissolution rate of nifedipine with correlation to the time elapsed (mean values of three points) are shown in FIG. 2.

As is obviously shown in FIG. 2, the preparation according to the present invention can provide a supersaturated solution which exceeds the saturated solubility of nifedipine (Comparative Example 2), and maintain the supersaturated concentration without a decrease with correlation to the time elapsed. Also it has been shown hat preparation of the present invention has a drug solubility improvement effect comparative to that of the preparation (Comparative Example 1) by the solvent method using an organic solvent of which the effect has been confirmed.

What is claimed is:

1. A process for producing a pharmaceutical solid preparation, comprising spraying
   a solution wherein a poorly soluble drug is dissolved in a plasticizer; and
   at least one of an aqueous solution and a water dispersion of a water-soluble polymer,
   from nozzle outlets simultaneously and separately.

2. The process for producing the pharmaceutical solid preparation according to claim 1, wherein said plasticizer is selected from a group consisting of citrate esters, glycerine esters, phthalate esters and polyvalent alcohols.

3. The process for producing the pharmaceutical solid preparation according to claim 1, wherein said water-soluble polymer is selected from the group consisting of cellulose derivatives and poly(vinylpyrrolidone).

4. The process for producing the pharmaceutical solid preparation according to claim 2, wherein said water-soluble polymer is selected from the group consisting of cellulose derivatives and poly(vinylpyrrolidone).

5. The process for producing a pharmaceutical solid preparation according to claim 1, wherein 1,000 ml of a solvent or greater is needed to dissolve 1 g or 1 ml of the poorly soluble drug.

6. The process for producing a pharmaceutical solid preparation according to claim 1, wherein the poorly soluble drug is selected from the group consisting of nifedipine, phenacetin, phenytoin, digitoxin, nilvadipine, diazepam, griseofulvin and chloramphenicol.

* * * * *